(12) United States Patent
Tada et al.

(10) Patent No.: US 7,795,300 B2
(45) Date of Patent: Sep. 14, 2010

(54) EXTERNAL PREPARATION FOR SKIN

(75) Inventors: Akihiro Tada, Yokohama (JP); Akiko Kanamaru, Yokohama (JP)

(73) Assignees: Kuraray Co., Ltd., Okayama (JP); Pola Chemical Industries Inc., Shizuoka (JP)

( * ) Notice: Subject to any disclaimer, the term of this patent is extended or adjusted under 35 U.S.C. 154(b) by 1142 days.

(21) Appl. No.: 10/580,882

(22) PCT Filed: Dec. 14, 2004

(86) PCT No.: PCT/JP2004/018649

§ 371 (c)(1),
(2), (4) Date: May 26, 2006

(87) PCT Pub. No.: WO2005/055962

PCT Pub. Date: Jun. 23, 2005

(65) Prior Publication Data

US 2007/0105947 A1 May 10, 2007

(30) Foreign Application Priority Data

Dec. 15, 2003 (JP) ............................. 2003-416942

(51) Int. Cl.
*A01N 43/16* (2006.01)
*A61K 31/35* (2006.01)
*C07D 311/00* (2006.01)
*A61Q 5/08* (2006.01)
*A61Q 19/02* (2006.01)

(52) U.S. Cl. ..................... 514/456; 549/402; 424/62
(58) Field of Classification Search .................. 514/456; 549/402; 424/62
See application file for complete search history.

(56) References Cited

U.S. PATENT DOCUMENTS

2006/0147398 A1  7/2006  Tada

FOREIGN PATENT DOCUMENTS

| DE | 42 27 806 | 2/1993 |
|---|---|---|
| EP | 1 147 764 | 10/2001 |
| JP | 55-111411 | 8/1980 |
| JP | 57-035506 | 2/1982 |
| JP | 60-104005 | 6/1985 |
| JP | 05-004905 | 1/1993 |
| JP | 07-004905 | 1/1993 |
| JP | 07-002643 | 1/1995 |
| JP | 07-025762 | 1/1995 |
| JP | 07002643 A * | 1/1995 |
| JP | 08-048620 | 2/1996 |
| JP | 08-104646 | 4/1996 |
| JP | 10-287544 | 10/1998 |
| JP | 11-246339 | 9/1999 |
| JP | 11-246347 | 9/1999 |
| JP | 11246339 A * | 9/1999 |
| JP | 11-349435 | 12/1999 |
| JP | 2000-016917 | 1/2000 |
| JP | 2000-038334 | 2/2000 |
| JP | 2000-502359 | 2/2000 |
| JP | 2001-010926 | 1/2001 |
| JP | 2001-316214 | 11/2001 |
| JP | 2002-003363 | 1/2002 |
| JP | 2002-020225 | 1/2002 |
| JP | 2002-179516 | 6/2002 |
| JP | 2002-241213 | 8/2002 |
| JP | 2003-081807 | 3/2003 |
| JP | 2003-113027 | 4/2003 |
| JP | 2003-212714 | 7/2003 |
| JP | 2004-250354 | 9/2004 |
| WO | WO 98/07406 | 2/1998 |
| WO | WO 2004/050054 | 6/2004 |

OTHER PUBLICATIONS

Katagiri, et al. "Inhibitory Action of $-N-Butylresorcinol (Rucinol) on Melanogenesis and Its Skin Whitening Effects," Chemical Abstracts Service, Columbus Ohio, Aug. 2, 2001.
European Search Report dated Apr. 20, 2005.
International Search Report dated Mar. 11, 2005.
Glasl, et al. "Sesquiterpenes and Flavonoid Aglycones from a Hungarian Taxon of the *Achillea millefolium* Group," *A. Naturforsch*, 2002(11-12), pp. 976-982.
Takeda, et al., ed. *Usefulness of Cosmetics. Advances and Future Perspective in Evaluation Technology*, The Yakuji Nippo Limited, Mar. 31, 2001, Partial.
Notice of Reason for Rejection issued in the corresponding Japanese patent application No. 2004-357952 and mailed Jan. 12, 2010 (with English translation).

* cited by examiner

*Primary Examiner*—Sreeni Padmanabhan
*Assistant Examiner*—Kendra D Carter
(74) *Attorney, Agent, or Firm*—Knobbe, Martens, Olson & Bear, LLP

(57) ABSTRACT

The present invention relates to an external preparation for skin comprising a compound, such as centaureidin(5,7-dihydroxy-3,6-dimethoxy-2-(5-hydroxy-4-methoxyphenyl)-4H-1-benzopyran-4-one); 5,7-dihydroxy-3,6,8-trimethoxy-2-(3,4,5-trihydroxyphenyl)-4H-1-benzopyran-4-one; 3,5-diethoxy-6,7-dimethoxy-2-(5-ethoxy-4-methoxyphenyl)-4H-1-benzopyran-4-one; and 5,6-dihydroxy-3,7-dimethoxy-2-(5-hydroxy-2,4-dimethoxyphenyl)-4H-1-benzopyran-4-one; and/or salt thereof and 4-n-butyl resorcinol and/or a salt thereof.

The present invention provides an external preparation for skin having a function as a substantial lightening cosmetic that exerts whitening action of inhibiting excessive melanin production and keeping natural-looking whiteness.

5 Claims, No Drawings

EXTERNAL PREPARATION FOR SKIN

RELATED APPLICATIONS

This application is the U.S. National Phase under 35 U.S.C. §371 of International Application PCT/JP2004/018649, filed Dec. 14, 2004, which was published in a language other than English and which claims priority to JP 2003-416942, filed Dec. 15, 2003.

TECHNICAL FIELD

The present invention relates to an external preparation for skin, and more specifically to an external preparation for skin useful for a lightening cosmetic.

BACKGROUND ART

Many people desire to keep skin color white. On the other hand, there are also people who have a resistance to strange whiteness of skin or uncomfortable whiteness of skin that has appeared owing to the recently developed various kinds of whitening cosmetics. Accordingly, whitening to become a fair-complexioned and natural-looking white skin has been desired. As for external preparations for skin for this purpose, the field of cosmetics called "lightening cosmetics" has recently become common (see, for example, Patent documents 1, 2, and 3). However, although the concept of lightning cosmetics has been built, because there was no active ingredient responsible for the substance, the situation has been where it must be said that there is no effective lightening cosmetic. In order to obtain such an effect, it is said that a lightening cosmetic needs to have a not excessive but appropriate inhibitory effect on melanin production, an excellent skin conditioning effect, and an excellent moisturizing effect in combination. However, such a material and a combination of components providing such effects have not been known yet.

Examples of a "whitening agent" that is a component inhibiting melanin production and has already been developed include: placenta extract; ellagic acid and salts thereof; ascorbic acid and derivatives thereof; tranexamic acid and salts thereof; kojic acid and salts thereof; arbutin and salts thereof; and 4-n-butyl resorcinol and salts thereof (see, for example, Non-patent document 1).

An extremely small amount of centaureidin, which is one of the compounds represented by the following general formula (1), is known to be present in a plant of the genus *Achillea* sp. of the family Compositae, such as *Achillea millefolium* (see, for example, Non-patent document 2). Moreover, it has already been known that a component of a plant of the genus *Achillea* sp. of the family Compositae, such as *Achillea millefolium*, has whitening action (see, for example, Patent documents 4, 5, and 6). It has also already been known that whitening is achieved by inhibiting elongation of dendrites of melanocytes (see, for example, Patent documents 7 and 8).

[Non-patent document 1] Takeda et al. ed., "Usefulness of Cosmetics. Advances and Future Perspective in Evaluation Technology. (Keshohin no Yuyosei. Hyokagijyutsu no Shimpo to Shoraitembo.)", The Yakuji Nippo Limited, Mar. 31, 2001.

[Non-patent document 2] Glasl S., et al., Z. Naturforsch., 2002(11-12), 976-982

[Patent document 1] JP 2003-212714 A
[Patent document 2] JP 2000-502359 A
[Patent document 3] JP 08-48620 A
[Patent document 4] JP 08-104646 A
[Patent document 5] JP 11-349435 A
[Patent document 6] JP 2001-316214 A
[Patent document 7] JP 2003-113027 A
[Patent document 8] JP 2003-81807 A

DISCLOSURE OF THE INVENTION

The present invention has been accomplished under the circumstances as described above, and an object of the present invention is to provide an external preparation for skin having a function as a substantial lightening cosmetic that exerts whitening action of inhibiting excessive melanin production and keeping natural-looking whiteness.

In order to solve the above problems, the inventors of the present invention have carried out intensive studies to obtain an external preparation for skin having a function as a substantial lightening cosmetic. As a result, we have found that an external preparation for skin containing a compound represented by the following general formula (1) and/or salt thereof and 4-n-butyl resorcinol and/or a salt thereof has desired characteristics. Thus, we have accomplished the present invention.

More specifically, the present invention relates to the following technology.

(1) An external preparation for skin, comprising a compound represented by the following general formula (1) (hereafter may be referred to as "Compound (A)") and/or salt thereof and 4-n-butyl resorcinol and/or a salt thereof.

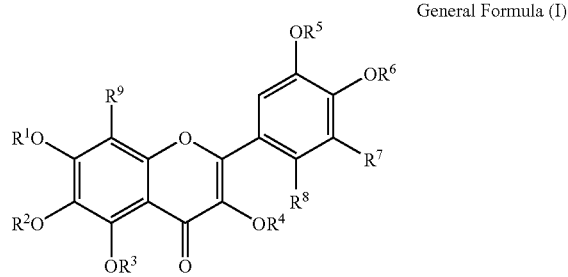

General Formula (I)

(In the formula, $R^1$, $R^2$, $R^3$, $R^4$, $R^5$, and $R^6$ each independently represent a hydrogen atom or an alkyl group having 1 to 4 carbon atoms, and $R^7$, $R^8$, and $R^9$ each independently represent a hydrogen atom, a hydroxyl group, or an alkyloxy group having 1 to 4 carbon atoms.)

(2) The external preparation for skin according to (1), wherein the compound represented by the general formula (I) is one or two or more selected from 5,7-dihydroxy-3,6-dimethoxy-2-(5-hydroxy-4-methoxyphenyl)-4H-1-benzopyran-4-one, 5,7-dihydroxy-3,6,8-trimethoxy-2-(3,4,5-trihydroxyphenyl)-4H-1-benzopyran-4-one, 3,5-diethoxy-6,7-dimethoxy-2-(5-ethoxy-4-methoxyphenyl)-4H-1-benzopyran-4-one, and 5,6-dihydroxy-3,7-dimethoxy-2-(5-hydroxy-2,4-dimethoxyphenyl)-4H-1-benzopyran-4-one.

(3) The external preparation for skin according to (1) or (2), wherein a source of the compound represented by the general formula (1) and/or salt thereof is an extract of a plant of the genus *Achillea* sp. of the family Compositae or the genus *Centaurea* sp. of the family Compositae.

(4) The external preparation for skin according to (3), wherein the plant of the genus *Achillea* sp. of the family Compositae is selected from *Achillea ageratum*, *Achillea cartilaginea*, *Achillea clavenae*, *Achillea filipendula*, *Achillea millefo-*

*lium*, *Achillea nana*, *Achillea ptarmica*, and *Achillea tomentosa*, and the plant of the genus *Centaurea* sp. of the family Compositae is *Centaurea cyanus*.

(5) The external preparation for skin according to any one of (1) to (4), wherein a concentration of the compound represented by the general formula (1) and/or salt thereof is 0.1 mM or higher.

(6) The external preparation for skin according to any one of (1) to (4), wherein a content of the compound represented by the general formula (1) and/or salt thereof is 0.035% by mass or higher.

(7) The external preparation for skin according to any one of (1) to (6), wherein a content of 4-n-butyl resorcinol and/or the salt thereof is in a range of 0.05 to 5% by mass.

(8) The external preparation for skin according to any one of (1) to (7), wherein the external preparation for skin is a whitening cosmetic.

(9) The external preparation for skin according to (8), wherein the external preparation for skin is a lightening cosmetic.

BEST MODE FOR CARRYING OUT THE INVENTION

According to the present invention, a "lightening cosmetic" exerting whitening action of inhibiting excessive melanin production and keeping natural-looking whiteness can be realized.

Hereinafter, the present invention will be described in detail.

In the present invention, the meaning of "natural-looking white skin" is not a skin of which color is too white and loses a feeling of reality of skin, but a skin which has a feeling of reality as a skin of a person alive and causes a feeling of whiteness of skin in an appearance as a whole. Specifically, the "natural-looking white skin" throughout the mankind refers to a skin showing a color of which Hue is kept in a range from 10.0 R to 5.0 YR in Munsell's chromaticity coordinate and Value is improved to 3 to 7. The "natural-looking white skin" in the yellow race such as Japanese refers to a skin showing a color of which Hue is kept in a range from 10.0 R to 5.0 YR and Value is improved to 6 to 7. Chroma becomes in a range from 2.8 to 4.2. The value of Chroma usually does not fluctuate by a treatment of cosmetics or the like.

The Munsell's chromaticity coordinate is a color system expressing a color by three axes of Value (V), Chroma (C) and Hue (H) designed by H. A. Munsell. It is said that Munsell's chromaticity coordinate is superior in an expression of sensual color recognition of human. It is generally known that a color is expressed by a combination of three independent stimulus values. Such color system using the combination of three stimulus values can be exemplified by RGB color system, XYZ color system or the like. However, it is said that when using the Munsell's chromaticity coordinate, it is easiest to image a color sensually from a chromaticity coordinate (The COLOR SCIENCE ASSOCIATION OF JAPAN ed., "Color Science Handbook New Edition. (Sinpen Sikisai Kagaku Handbook.)", University of Tokyo Press, Sep. 10, 1985.).

<1> About a Compound (A) and/or Salt Thereof, each of which is an Essential Ingredient of an External Preparation for Skin According to the Present Invention An external preparation for skin according to the present invention contains a compound (A) and/or salt thereof. In the general formula (1), $R^1$, $R^2$, $R^3$, $R^4$, $R^5$, and $R^6$ each independently represent a hydrogen atom or an alkyl group. The alkyl group is preferably an alkyl group having 1 to 4 carbon atoms, and examples thereof include methyl group, ethyl group, propyl group, 1-methylethyl group, n-butyl group, 1-methylpropyl group, 2-methylpropyl group, and 1,1-dimethylethyl group. Of those alkyl groups, methyl group and ethyl group are particularly preferred. Moreover, $R^7$, $R^8$, and $R^9$ each independently represent a hydrogen atom, a hydroxyl group, or an alkyloxy group. The alkyloxy group is preferably an alkyloxy group having 1 to 4 carbon atoms, and examples thereof include methoxy group, ethoxy group, propyloxy group, 1-methylethyloxy group, n-butyloxy group, 1-methylpropyloxy group, 2-methylpropyloxy group, and 1,1-dimethylethyloxy group. Of those alkyloxy groups, methoxy group is particularly preferred.

Specific examples of the compound (A) as described above preferably include: centaureidin (5,7-dihydroxy-3,6-dimethoxy-2-(5-hydroxy-4-methoxyphenyl)-4H-1-benzopyran-4-one, hereafter referred to as "Compound 1"); 5,7-dihydroxy-3,6,8-trimethoxy-2-(3,4,5-trihydroxyphenyl)-4H-1-benzopyran-4-one (hereafter referred to as "Compound 2"); 3,5-diethoxy-6,7-dimethoxy-2-(5-ethoxy-4-methoxyphenyl)-4H-1-benzopyran-4-one (hereafter referred to as "Compound 3"); and 5,6-dihydroxy-3,7-dimethoxy-2-(5-hydroxy-2,4-dimethoxyphenyl)-4H-1-benzopyran-4-one (hereafter referred to as "Compound 4"). Of those compounds, Compound 1 is particularly preferred. In addition, each of those compounds may be used singly or two or more of them may be used in combination. Furthermore, preferable examples of salts of the compound (A) include: alkali metal salts such as sodium salt and potassium salt; alkaline earth metal salts such as calcium salt and magnesium salt; ammonium salt; organic amine salts such as triethanolamine salt and triethylamine salt; and basic amino acid salts such as lysine salt and arginine salt. The compound (A) and/or salt thereof have inhibitory action on elongation of dendrites of melanocytes. By the combination of this action and inhibitory action on melanin production, the external preparation for skin according to the present invention exerts a whitening effect without inhibiting melanin production excessively. Therefore, whitening without losing natural-looking whiteness can be realized.

A compound (A) and/or salt thereof for use in the present invention may be a purified one, and it may be an extract of a plant or fraction thereof containing the compound (A) and/or salt thereof in an effective amount. Examples of such plants include plants belonging to the genus *Achillea* sp. of the family Compositae and plants belonging to the genus *Centaurea* sp. of the family Compositae. A plant for use in extraction of the compound (A) and/or salt thereof may be a whole plant body, may be a portion containing the compound (A) and/or salt thereof, or may be a processed product of these. For instance, Compound 1 can be obtained by purifying and fractionating an extract of the above ground portion of a plant of the genus *Achillea* sp. of the family Compositae. Identification of Compound 1 can be carried out by High Performance Liquid Chromatography (HPLC) using a standard substance mentioned below. Moreover, other compounds (A) can also be identified in a similar manner.

Particularly preferable examples of an extract of *Achillea millefolium* include an extract extracted with a solvent. Preferable examples of solvents include: ethers such as diethyl ether, isopropyl ether, and tetrahydrofuran; halogenated hydrocarbons such as methylene chloride and chloroform; esters such as ethyl acetate and methyl formate; ketones such as acetone and methyl ethyl ketone; nitrites such as acetonitrile; alcohols such as 1,3-butanediol, ethanol, and isopropyl alcohol; and water. Of those, alcohols are more preferred, and ethanol is particularly preferred. In addition, each of the above solvents may be used singly or two or more of them may be used in combination.

Extraction can be carried out by adding a solvent having a mass of 1 to 10 times that of a plant body, preferably a dried plant body thereto to immerse the plant body therein for several days at room temperature or for several hours at a temperature around the boiling point. After extraction, if necessary, it is preferable to remove the solvent by means of vacuum concentration or the like. The extract from which the solvent has been removed is subjected to liquid-liquid extraction with ethyl acetate and water, or the like or purified by, for example, silica gel column chromatography using chloroform-methanol as an eluting solvent. Alternatively, the extract is dispersed in water and the dispersion is charged into a column filled with an ion-exchange resin (for example, DIAION (registered trademark) HP-20, manufactured by Mitsubishi Chemical Corporation). After water is run through the column, elution with a solvent such as an alcohol or the like is carried out and then the solvent is distilled away from the eluate. Accordingly, an extract containing the above Compound 1 at a content of 1 to 20% by mass can be produced.

Examples of the above plants of the genus *Achillea* sp. of the family Compositae include *Achillea ageratum, Achillea cartilaginea, Achillea clavenae, Achillea filipendula, Achillea millefolium, Achillea nana, Achillea ptarmica*, and *Achillea tomentosa*. Any of those contains Compound 1 in a small amount, therefore the same treatment as that in Achillea millefolium described above enables production of an extract containing Compound 1 at a content of 1 to 20% by mass.

Concerning Compounds 2, 3, and 4, an extract containing any of the above compounds or a mixture of these at a content of 1 to 10% by mass can be produced by performing the above-mentioned extract operation, replacing a plant of the genus *Achillea* sp. of the family Compositae with a plant of the genus *Centaurea* sp. of the family Compositae.

The preferable content of the compound (A) and/or salt thereof purified from the extract obtained as described above is 0.003% by mass or higher in total, more preferably 0.02% by mass or higher for the total amount of an external preparation for skin. In addition, the preferable upper limit of the content of the compound (A) and/or salt thereof is 2% by mass or lower in total, more preferably 1% by mass or lower for the total amount of an external preparation for skin. This is because there are cases where too small a content of the compound (A) and/or salt thereof results in no effect and cases where the effect reaches the peak and too much of the compound (A) and/or salt thereof provides no more effect. Further, there are cases where too much of the extract impairs the stability of the preparation.

PRODUCTION EXAMPLE 1 TO 5

10 kg of dried pieces of the above ground portion of a plant of the genus *Achillea* sp. of the family Compositae described in Table 1 were shredded and 50 L of ethanol were added thereto, and the mixture was heated under reflux for 3 hours. After cooling down to room temperature, the mixture was concentrated under reduced pressure. 1 L of ethyl acetate and water was added thereto, followed by liquid-liquid extraction. The ethyl acetate phase was collected and concentrated under reduced pressure. The residue was dispersed in water and then the dispersion was charged into a column filled with an above-mentioned ion-exchange resin 'HP-20'. After 3 L of water had been run off through the column, the adsorbed component was eluted with 1 L of ethanol from the column. The eluate was concentrated under reduced pressure to thereby obtain an extract. The amount of Compound 1 (Centaureidin) in the extract was determined with an absolute calibration curve using a standard substance (obtained by recrystallizing an isolated product from isopropyl alcohol and identifying by means of $^1$H-NMR) by HPLC (column: ODS, manufactured by Shimadzu Corporation, eluate: 30% acetonitrile aqueous solution, detection: UV 220 nm).

TABLE 1

Extracts and content of centaureidin

| Production Examples | Plant | Yield of extract (%) | Centaureidin content in extract (% by mass) |
|---|---|---|---|
| 1 | *Achillea ageratum* | 9.7 | 13.1 |
| 2 | *Achillea cartilaginea* | 5.3 | 7.9 |
| 3 | *Achillea millefolium* | 8.5 | 14.4 |
| 4 | *Achillea nana* | 5.9 | 9.2 |
| 5 | *Achillea tomentosa* | 7.3 | 7.6 |

PRODUCTION EXAMPLE 6

1 g of the extract of *Achillea millefolium* obtained in Production Example 3 was further purified by means of silica gel column chromatography (column: Wakogel (registered trademark) C-100 (model number), manufactured by Wako Pure Chemical Industries, Ltd., eluting solvent: chloroform:methanol=100:0 to 90:10) to thereby obtain 43 mg of Compound 1. Identification and determination of Compound 1 in the eluate were carried out in a similar manner as in the determination by means of HPLC in Production Examples 1 to 5.

PRODUCTION EXAMPLE 7

In the same manner as in Production Example 1, 10 kg of dried pieces of the above ground portion of *Centaurea cyanus* of the genus *Centaurea* sp. of the family Compositae were shredded and 50 L of ethanol were added thereto, and the mixture was heated under reflux for 3 hours. After cooling down to room temperature, the mixture was concentrated under reduced pressure. 1 L of ethyl acetate and water was added thereto, followed by liquid-liquid extraction. The ethyl acetate phase was collected and concentrated under reduced pressure. The residue was dispersed in water and then the dispersion was charged into a column filled with an above-mentioned ion-exchange resin 'HP-20'. After 3 L of water had been run off through the column, the adsorbed component was eluted with 1 L of ethanol from the column. The eluate was concentrated under reduced pressure to thereby obtain an extract. 1 g of this extract was further purified by means of silica gel column chromatography (eluting solvent: chloroform:methanol=100:0 to 90:10) to thereby obtain 71 mg of Compound 2, 10.6 mg of Compound 3, and 59.1 mg of Compound 4. Identification and determination of each compound in the eluate were carried out in a similar manner as in the determination by means of HPLC in Production Examples 1 to 5.

<2> About 4-n-butyl Resorcinol and/or a Salt Thereof, each of which is an Essential Ingredient of an External Preparation for Skin According to the Present Invention An external preparation for skin according to the present invention contains 4-n-butyl resorcinol and/or a salt thereof (hereafter referred to as "4-n-butyl resorcinol and the like"). It is known that 4-n-butyl resorcinol and the like are whitening ingredients that inhibit melanin production (see, for example, the above Non-patent document 1).

4-n-butyl resorcinol can be produced according to a conventional method. For instance, 4-n-butyl resorcinol can be produced according to a method described in Lille, J.; Bitter, L. A.; Peiner, V. Trudy-Nauchono-Issledovatel' skii Institut Slantsev (1969), No. 18, 127-34. More specifically, it can be exemplified a method involving: condensing resorcin and butanoic acid in the presence of zinc chloride and reducing the condensed product with zinc amalgam/hydrochloric acid, or a method involving condensing resorcin and n-butyl alcohol at 200 to 400° C.

4-n-butyl resorcinol thus obtained can be allowed to react with various basic compounds to form salts. Such salts are not particularly limited so long as they are physiologically acceptable, and preferable examples thereof include: alkali metal salts such as sodium salt and potassium salt; alkaline earth metal salts such as calcium salt and magnesium salt; ammonium salt; organic amine salts such as triethanolamine salt and triethylamine salt; and basic amino acid salts such as lysine salt and arginine salt. Of those salts, alkali metal salts are particularly preferred, and of those, a sodium salt is particularly preferred.

An external preparation for skin according to the present invention may contain one kind of 4-n-butyl resorcinol and the like singly or may contain two or more kinds thereof in combination.

The preferable content of 4-n-butyl resorcinol and the like in an external preparation for skin according to the present invention is preferably 0.05 to 5% by mass in total, more preferably 0.1 to 3% by mass for the total amount of the external preparation for skin. This is because there are cases where too little of the compound results in no effect and cases where the effect reaches the peak and too much of the compound provides no more effect.

<3> About an External Preparation for Skin According to the Present Invention

An external preparation for skin according to the present invention contains a compound (A) and/or salt thereof and 4-n-butyl resorcinol and the like. The external preparation for skin according to the present invention can contain optional ingredients used commonly in an external preparation for skin in addition to those essential ingredients.

Preferred examples of such an optional ingredient include: oils and waxes such as macadamia nut oil, avocado oil, corn oil, olive oil, rapeseed oil, sesame oil, castor oil, safflower oil, cottonseed oil, jojoba oil, coconut oil, palm oil, liquid lanolin, hydrogenated coconut oil, hydrogenated oil, haze wax, hydrogenated castor oil, beeswax, candelilla wax, carnauba wax, insect wax, lanolin, reduced lanolin, hard lanolin, and jojoba wax; hydrocarbons such as liquid paraffin, squalane, pristane, ozokerite, paraffin, ceresin, vaseline, and microcrystalline wax; higher fatty acids such as oleic acid, isostearic acid, lauric acid, myristic acid, palmitic acid, stearic acid, behenic acid, and undecylenic acid; alcohols such as ethanol, isopropanol, cetyl alcohol, stearyl alcohol, isostearyl alcohol, behenyl alcohol, octyldodecanol, myristyl alcohol, and cetostearyl alcohol; oils such as silicone oils including linear polysiloxanes such as dimethyl polysiloxane, methylphenyl polysiloxane, and diphenyl polysiloxane, cyclic polysiloxanes such as octamethylcyclotetrasiloxane, decamethylcyclopentasiloxane, and dodecamethylcyclohexasiloxane, and modified polysiloxanes such as amino-modified polysiloxane, polyether-modified polysiloxane, alkyl-modified polysiloxane, and fluorine-modified polysiloxane;

anionic surfactants such as fatty acid soaps (including sodium laurate and sodium palmitate), potassium lauryl sulfate, and triethanolamine alkyl ether sulfate; cationic surfactants such as stearyltrimethylammonium chloride, benzalkonium chloride, and laurylamine oxide; amphoteric surfactants such as an imidazoline-based amphoteric surfactants (including 2-cocoyl-2-imidazolinium hydroxide-1-carboxyethyloxy-2-sodium), a betaine-based amphoteric surfactants (including alkyl betaine, amide betaine, and sulfobetaine), and acylmethyl taurine; synthetic ester oils such as cetyl isooctanoate, isopropyl myristate, hexyldecyl isostearate, diisopropyl adipate, di-2-ethylhexyl sebacate, cetyl lactate, diisostearyl malate, ethylene glycol di-2-ethyl hexanoate, neopentyl glycol dicaprate, glycerin di-2-heptyl undecanoate, glycerin tri-2-ethylhexanoate, trimethylolpropane tri-2-ethyl hexanoate, trimethylolpropane triisostearate, and pentaerythritol tetra-2-ethylhexanoate; nonionic surfactants such as sorbitan fatty acid esters (including sorbitan monostearate and sorbitan sesquioleate), glycerin fatty acids (including glycerin monostearate), propylene glycol fatty acid esters (including propylene glycol monostearate), hydrogenated castor oil derivatives, glycerinalkyl ethers, polyoxyethylene (POE) sorbitan fatty acid esters (including POE sorbitan monooleate and polyoxyethylenesorbitanmonostearate), POE sorbit fattyacidesters (including POE-sorbitanmonolaurate), POE glycerin fatty acid esters (including POE-glycerin monoisostearate), POE fatty acid esters (including polyethylene glycol monooleate and POE distearate), POE alkyl ethers (including POE2-octyldodecylether), POE alkylphenyl ethers (including POE nonylphenyl ether), Pluronics, POE-polyoxypropylene(POP) alkyl ethers (including POE-POP2-decyltetradecyl ether), Tetronics, a POE castor oil-hydrogenated castor oil derivatives (including POE castor oil and POE hydrogenated castor oil), sucrose fatty esters, and alkylglycosides;

polyalcohols such as polyethylene glycol, glycerin, 1,3-butanediol, erythritol, sorbitol, xylitol, maltitol, propylene glycol, dipropylene glycol, diglycerin, isoprene glycol, 1,2-pentanediol, 2-methyl-2,4-pentanediol, 1,2-hexanediol, 1,2-heptanediol, and 1,2-octanediol;

moisture components such as a polymer or copolymer in which polyacrylic acid or polymethacrylic acid is a base substance and a hydrophilic group is introduced as a side chain, such as, polymethacryloyloxyethylphosphorylcholine, polyglucosyloxyethylmethacrylate, and polymethacryloyl lysine, sodium pyrrolidone carboxylate, lactic acid, and sodium lactate;

thickeners such as guar gum, quince seed, carrageenan, galactan, gum arabic, pectin, mannan, starch, xanthan gum, curdlan, methylcellulose, hydroxyethylcellulose, carboxymethylcellulose, methylhydroxypropylcellulose, chondroitin sulfate, dermatan sulfate, glycogen, heparan sulfate, hyaluronic acid, sodium hyaluronate, tragacanth gum, keratansulfate, chondroitin, mucoitin sulfate, hydroxyethyl guar gum, carboxymethyl guar gum, dextran, keratosulfate, locustbeangum, succinoglucan, charonicacid, chitin, chitosan, carboxymethyl chitin, agar, polyvinyl alcohol, polyvinyl pyrrolidone, carboxyvinyl polymer, sodium polyacrylate, polyethylene glycol, and bentonite;

preservatives such as phenoxyethanol;

powders such as mica, talc, kaolin, synthetic mica, calcium carbonate, magnesium carbonate, silicic anhydride (silica), aluminum oxide, and barium sulfate which may have treated surfaces;

inorganic pigments such as colcothar, yellow iron oxide, black iron oxide, cobalt oxide, ultramarine blue pigment, iron blue pigment, titanium oxide, and zinc oxide which may have treated surfaces;

pearls such as mica titanium, fish scale guanine, and bismuth oxychloride which may have treated surfaces;

organic pigments such as Red 202, Red 228, Red 226, Yellow 4, Blue 404, Yellow 5, Red 505, Red 230, Red 223, Orange 201, Red 213, Yellow 204, Yellow 203, Blue 1, Green 201, Violet 201, and Red 204 which may be laked;

organic powders such as polyethylene powder, methyl polymethacrylate powder, nylon powder, and organopolysiloxane elastomer powder; UV absorbers such as p-aminobenzoic acid-based UV absorber, anthranilic acid-based UV absorber, salicylic acid-based UV absorber, cinnamic acid-based UV absorber, benzophenone-based UV absorber, 2-(2'-hydroxy-5'-t-octylphenyl)benzotriazole, and 4-methoxy-4'-t-butyl dibenzoylmethane;

and vitamins such as vitamin A and derivatives thereof, vitamin Bs including vitamin $B_6$ hydrochloride, vitamin $B_6$ tripalmitate, vitamin $B_6$ dioctanoate, vitamin $B_2$ and derivatives thereof, vitamin $B_{12}$, and vitamin $B_{15}$ and derivatives thereof, vitamin Es including α-tocopherol, β-tocopherol, δ-tocopherol, and vitamin E acetate, vitamin Ds, vitamin H, pantothenic acid, pantethine, and pyrroloquinoline quinone.

An external preparation for skin according to the present invention can be produced by processing those optional ingredients and the above essential ingredients according to a conventional method.

In addition, an external preparation for skin according to the present invention may contain a whitening ingredient except 4-n-butyl resorcinol and the like so long as the effects of the combination of a compound (A) and/or salt thereof and 4-n-butyl resorcinol and the like are not impaired.

An external preparation for skin according to the present invention can be applied to any composition without particular limitation so long as it is a composition of a kind in a form to be administered externally on the skin. Preferable applications include external drugs for skin, cosmetics, and sundry goods, and it is particularly preferable to apply to a cosmetic. A whitening cosmetic is preferred as a cosmetic, and a so-called lightening cosmetic is particularly preferred as a whitening cosmetic. This is because of the characteristic of natural-looking whitening action (lightening action) that an external preparation for skin according to the present invention has. The dosage form of an external preparation for skin according to the present invention is not particularly limited, and examples thereof include lotion, extract, emulsion, and cream.

Of the above optional ingredients, particularly preferable ingredients are, first, antibacterial polyalcohols such as 1,3-butanediol, isoprene glycol, 1,2-pentanediol, 2-methyl-2,4-pentanediol, 1,2-hexanediol, 1,2-heptanediol, and 1,2-octanediol, and second, a polymer or copolymer in which polyacrylic acid or polymethacrylic acid is a base substance and a hydrophilic group is introduced as a side chain, such as polymethacryloyloxyethylphosphorylcholine, poly(glucosyloxyethyl methacrylate), and polymethacryloyllysine.

In the present invention, the meaning of the term "antibacterial" includes the strict meaning of "antibacterial" ("antimicrobial") and the meaning of "bacteriostatic" or "fungistatic". Polyalcohols having bactericidal action or inhibitory action on growth of microorganisms are "antibacterial" defined in the present invention. Antibacterial polyalcohols are not particularly limited so long as they do not impair the effect of the present invention. Examples thereof include linear alkyl diols each having a comparatively long carbon chain such as polyalcohols described above, and any of these can be used in an external preparation for skin according to the present invention. Of those, there can be more preferably mentioned one or two or more selected from 1,3-butanediol, isoprene glycol, 2-methyl-2,4-pentanediol, 1,2-pentanediol, 1,2-heptanediol, 1,2-hexanediol, and 1,2-octanediol. The content of a polyalcohol is preferably 1 to 10% by mass in total for the total amount of the external preparation for skin. The presence of such an ingredient enables a preparation to be produced without using a preservative such as paraben that may induce skin irritation. Accordingly, skin can be made smooth and a lightening effect can be improved.

With regard to a polymer or copolymer in which polyacrylic acid or polymethacrylic acid is a base substance and a hydrophilic group is introduced as a side chain, a polyacrylic acid structure can be used as a base substance, but a polymethacrylic acid structure is preferred as a base substance. Preferable examples of the above hydrophilic group include saccharide residues, amino acid residues, and groups each having a phosphoryl group. Such a polymer or copolymer can be obtained by polymerizing (meth)acrylic acid derivative obtained by reacting acrylic acid or methacrylic acid with acetylated saccharide or brominated saccharide; (meth)acrylic acid derivative obtained by inducing acrylic acid or methacrylic acid into acid chloride with thionyl chloride or the like and condensing the acid chloride with amino acid; or (meth)acrylic acid derivative obtained by esterifying chloroalcohol and acrylic acid or methacrylic acid and condensing the esterified product with amino acid or phosphorylcholine, or the like, if necessary, under the coexistence of a catalyst, by solution polymerization or the like. In addition, since any of those is commercially available, commercial products bought can be used. The preferable content of a polymer or copolymer in which polyacrylic acid or polymethacrylic acid is a base substance and a hydrophilic group is introduced as a side chain is 0.01 to 5% by mass in total for the total amount of an external preparation for skin. This ingredient has action of improving the water content of the surface of the skin to thereby exert a lightening effect more remarkably.

EXAMPLES

The present invention will be explained more specifically with reference to the following examples. However, it is needless to say that the scope of the present invention is not limited to these examples.

Test Example 1

Inhibitory Action on Elongation of Dendrites

According to the following method, inhibitory action on elongation of dendrites was examined using human melanocytes.

(Reagent and the like)

The following cell, basic medium, and reagents were purchased from Kurabo Industries Ltd.

(Cell) Normal human melanocytes (Medium) Basic medium (Medium 154S) to which the following reagents were added (Reagent) Growth additive: bovine pituitary extract (BPE) (final concentration in the medium: 0.4% v/v), fetus bovine serum (FBS) (final concentration in the medium: 0.5% v/v), human recombinant basic fibroblast growth factor (rFGF-B) (final concentration in the medium: 3 ng/ml), hydrocortisone (final concentration in the medium: 0.18 μg/ml), insulin (final concentration in the medium: 5 μg/ml), transferrin (final concentration in the medium: 5 μg/ml), phorbol 12-myristate 13-acetate (PMA) (final concentration in the medium: 10 ng/ml), heparin (final concentration in the medium: 3 μg/ml), PSA solution (mixed solution at a concentration of penicillin: 50,000 Unit/ml, a concentration of streptomycin: 50 μg/ml, and a concentration of amphotericin B: 12.5 μg/ml. Added 1 ml thereof for 500 ml of the medium.)

(Test Method)

Normal human melanocytes were seeded (3,000 cells/well) into a 48-well microplate into which the above medium (198 μl/well) was poured, and cultured at 37° C. After 24 hours, Compound 1 (centaureidin) produced in Production Example 6 was dissolved in dimethyl sulfoxide (DMSO) at final concentrations in the medium of 0 mM (control), 0.1 mM, 0.5 mM, and 1 mM, to obtain sample solutions. To 1 μl of each of those sample solutions, 9 μl of the medium were added. 2 μl of each solution were added into each well of the microplate and culture was continued. After 24 hours from addition of the samples, the length of dendrites was observed.

(Result)

The results are shown in Table 2. In the control (0 mM), dendrites elongate by an addition effect of growth factor, but in Compound 1 (centaureidin)—added group, it is found that elongation of dendrites is inhibited. This action can be confirmed in the case where the concentration of Compound 1 (centaureidin) is at least 0.1 mM, and the action is found to be particularly remarkable when the concentration of centaureidin is over the boundary of 0.5 mM.

TABLE 2

Inhibitory action of Compound 1 (centaureidin) on elongation of dendrites

| Concentration of centaureidin (mM) | Length of dendrite (μm) |
| --- | --- |
| 0 | 140 ± 29 |
| 0.1 | 101 ± 15 |
| 0.5 | 26 ± 8 |
| 1 | 24 ± 6 |

Test Example 2

In the same manner as in Test Example 1, but using extracts produced in Production Examples 1 to 5, sample solutions were prepared so that the final concentration of Compound 1 (centaureidin) in the medium was 0.5 mM, to thereby examine inhibitory action on elongation of dendrites. The results are shown in Table 3. The results show that inhibitory action on elongation of dendrites can be achieved by addition of an extract so long as the extract secures a prescribed amount of Compound 1 (centaureidin).

TABLE 3

Inhibitory action of extract on elongation of dendrites Extracts

| Extract | Concentration of extract (% by mass) | Length of dendrite (μm) |
| --- | --- | --- |
| Extract produced in Production Example 1 | 0.17 | 28 ± 10 |
| Extract produced in Production Example 2 | 0.27 | 23 ± 6 |
| Extract produced in Production Example 3 | 0.15 | 24 ± 9 |
| Extract produced in Production Example 4 | 0.24 | 31 ± 8 |
| Extract produced in Production Example 5 | 0.28 | 29 ± 13 |

Test Example 3

In the same manner as in Test Example 1, Compounds 2 to 4 were further examined for inhibitory action on elongation of dendrites under the condition that the final concentration in the medium was 0.5 mM. The results are shown in Table 4. The results show that compounds (A) other than compound 1 (centaureidin) also have inhibitory action on elongation of dendrites.

TABLE 4

Inhibitory action of Compounds 2 to 4 on elongation of dendrites

| Compounds | Length of dendrite (μm) |
| --- | --- |
| Compound 2 | 34 ± 19 |
| Compound 3 | 47 ± 28 |
| Compound 4 | 31 ± 22 |

Test Example 4

The effect of the combination of a compound (A) and 4-n-butyl resorcinol was studied using melanoma B-16 cells (obtained from Tomita Laboratory at Tohoku University, School of Medicine). MEM (modified Eagle's medium) supplemented with 15% FBS (fetal bovine serum) to which Compound 1 (centaureidin) and 4-butyl resorcinol at various concentrations were added was placed in each well of a microtiter plate. Melanoma B-16 cells were seeded into each well at a dose of $5 \times 10^5$ cells/ml and cultured for 48 hours. The cells were collected by means of centrifugal separation and washed twice with the medium, and then the color and number of the cells were judged using scores. Cells cultured without addition of both Compound 1 and 4-n-butyl resorcinol were used as a control, and judgment was carried out based on the following criteria: the color, score 0: the same as the control, score 1: slightly paler than the control, score 2: apparently paler than the control, score 3: cells were almost white, score 4: cells were white; the number of cells, score 0: almost all the cells were dead, score 1: nine-tenth of the cells were dead, score 2: about half the cells were dead, score 3: a few cells were dead, score 4: the number of cells was equal to that of the control. The results are shown in Table 5. The results show that the presence of Compound 1 inhibits cell death. Such action is in good accordance with inhibitory action of Compound 1 on dendrites of melanocytes.

TABLE 5

Effect of the combination of Compound 1 (centaureidin) and 4-n-butyl resorcinol

| Concentration of centaureidin (mM) | Concentration of 4-n-butyl resorcinol (% by mass) | Color of cells | Number of cells |
|---|---|---|---|
| 0 | 0 | Control | Control |
| 0 | 0.01 | score 1 | score 3 |
| 0 | 0.1 | score 3 | score 2 |
| 0 | 0.5 | score 4 | score 1 |
| 0.1 | 0 | score 1 | score 3 |
| 0.1 | 0.01 | score 1 | score 3 |
| 0.1 | 0.1 | score 4 | score 3 |
| 0.1 | 0.5 | score 4 | score 1 |
| 0.5 | 0 | score 1 | score 3 |
| 0.5 | 0.01 | score 2 | score 3 |
| 0.5 | 0.1 | score 4 | score 3 |
| 0.5 | 0.5 | score 4 | score 3 |

Example 1 and Comparative Example 1

According to the following prescription, a cosmetic of an external preparation for skin according to the present invention was produced. More specifically, the following prescribed ingredients were heated to 80° C. and stirred to solubilize each ingredient, and stirred and cooled to obtain Lotion 1. In the same manner, a lotion 1' of Comparative Example 1 in which Compound 1 in Lotion 1 was substituted with water was produced. Those lotions were given to five volunteer panelists (Japanese), and Lotion 1 was used for the right-half face and the lotion 1' of Comparative Example 1 was used for the left-half face twice a day for 80 consecutive days. They were asked which side was preferred, left or right, after the use test ended. As a result, all of the five answered that the right side was preferred. They said that the reason was natural-looking beautifulness (whiteness). Munsell values of skin of them are shown in Table 6. Color tone was measured with Spectrophotometer CD100, manufactured by Yokogawa M&C Corporation. As a result, Value was improved to 6 to 7 in each of the right-half faces and as to Hue a healthy skin color had been kept. On the contrary, Value was not sufficiently improved in each of the left-half faces and/or Hue of the skin was out of the range of that of a healthy skin. This shows that the external preparation for skin according to the present invention has whitening action that gives natural-looking appearance and is suitable for a lightening cosmetic.

TABLE 6

Whitening action of the Lotion 1

| Panelists (Japanese) | Right-half face | | | Left-half face | | |
|---|---|---|---|---|---|---|
| | Value | Hue | Chroma | Value | Hue | Chroma |
| A | 6.2 | 4.8 YR | 3.4 | 5.8 | 4.9 YR | 3.5 |
| B | 6.5 | 4.9 YR | 2.9 | 6.2 | 5.2 YR | 3.0 |
| C | 6.1 | 4.6 YR | 3.7 | 5.8 | 4.7 YR | 3.7 |
| D | 6.3 | 4.8 YR | 3.8 | 6.1 | 5.1 YR | 3.8 |
| E | 6.1 | 3.9 YR | 3.7 | 5.9 | 4.1 YR | 3.7 |

| | |
|---|---|
| 1,2-hexanediol | 3 parts by mass |
| 1,3-butanediol | 5 parts by mass |
| Glycerin | 2 parts by mass |
| Phenoxyethanol | 0.5 parts by mass |
| Compound 1 | 0.05 parts by mass |
| Polyoxyethylene hydrogenated castor oil | 0.1 parts by mass |
| Ethanol | 5 parts by mass |
| 4-n-butyl resorcinol | 0.3 parts by mass |
| Polymethacryloyllysine | 0.1 parts by mass |
| Polymethacryloyloxyethylphosphorylcholine | 0.1 parts by mass |
| Poly(glucosyloxyethyl methacrylate) | 0.1 parts by mass |
| Water | 83.75 parts by mass |

Example 2 and Comparative Example 2

In the same manner as in Example 1, but according to the following prescription, Lotion 2 as an external preparation for skin according to the present invention was produced. In the same manner, a lotion 2' of Comparative Example 2 in which Compound 2 in Lotion 2 was substituted with water was produced. Those lotions were given to five volunteer panelists (Japanese), and Lotion 2 was used for the right-half face and the lotion 2' of Comparative Example 2 was used for the left-half face twice a day for 80 consecutive days. They were asked which side was preferred, left or right, after the use test ended. As a result, all of the five answered that the right side was preferred. They said that the reason was natural-looking beautifulness (whiteness). This shows that the external preparation for skin according to the present invention has whitening action that gives natural-looking appearance and is suitable for a lightening cosmetic.

| | |
|---|---|
| 1,2-hexanediol | 3 parts by mass |
| 1,3-butanediol | 5 parts by mass |
| Glycerin | 2 parts by mass |
| Phenoxyethanol | 0.5 parts by mass |
| Compound 2 | 0.05 parts by mass |
| Polyoxyethylene hydrogenated castor oil | 0.1 parts by mass |
| Ethanol | 5 parts by mass |
| 4-n-butyl resorcinol | 0.3 parts by mass |
| Polymethacryloyllysine | 0.1 parts by mass |
| Polymethacryloyloxyethylphosphorylcholine | 0.1 parts by mass |
| Poly(glucosyloxyethyl methacrylate) | 0.1 parts by mass |
| Water | 83.75 parts by mass |

Example 3 and Comparative Example 3

In the same manner as in Example 1, but according to the following prescription, Lotion 3 as an external preparation for skin according to the present invention was produced. In the same manner, a lotion 3' of Comparative Example 3 in which Compound 3 in Lotion 3 was substituted with water was produced. Those lotions were given to five volunteer panelists (Japanese), and Lotion 3 was used for the right-half face and the lotion 3' of Comparative Example 3 was used for the left-half face twice a day for 80 consecutive days. They were asked which side was preferred, left or right, after the use test ended. As a result, all of the five answered that the right side was preferred. They said that the reason was natural-looking beautifulness (whiteness). This shows that the external preparation for skin according to the present invention has whitening action that gives natural-looking appearance and is suitable for a lightening cosmetic.

| | |
|---|---|
| 1,2-hexanediol | 3 parts by mass |
| 1,3-butanediol | 5 parts by mass |
| Glycerin | 2 parts by mass |
| Phenoxyethanol | 0.5 parts by mass |
| Compound 3 | 0.05 parts by mass |
| Polyoxyethylene hydrogenated castor oil | 0.1 parts by mass |
| Ethanol | 5 parts by mass |
| 4-n-butyl resorcinol | 0.3 parts by mass |
| Polymethacryloyllysine | 0.1 parts by mass |
| Polymethacryloyloxyethylphosphorylcholine | 0.1 parts by mass |
| Poly(glucosyloxyethyl methacrylate) | 0.1 parts by mass |
| Water | 83.75 parts by mass |

Example 4 and Comparative Example 4

In the same manner as in Example 1, but according to the following prescription, Lotion 4 as an external preparation for skin according to the present invention was produced. In the same manner, a lotion 4' of Comparative Example 4 in which Compound 4 in Lotion 4 was substituted with water was produced. Those lotions were given to five volunteer panelists (Japanese), and Lotion 4 was used for the right-half face and the lotion of Comparative Example 4 was used for the left-half face twice a day for 80 consecutive days. They were asked which side was preferred, left or right, after the use test ended. As a result, all of the five answered that the right side was preferred. They said that the reason was natural-looking beautifulness (whiteness). This shows that the external preparation for skin according to the present invention has whitening action that gives natural-looking appearance and is suitable for a lightening cosmetic.

| | |
|---|---|
| 1,2-hexanediol | 3 parts by mass |
| 1,3-butanediol | 5 parts by mass |
| Glycerin | 2 parts by mass |
| phenoxyethanol | 0.5 parts by mass |
| Compound 4 | 0.05 parts by mass |
| Polyoxyethylene hydrogenated castor oil | 0.1 parts by mass |
| Ethanol | 5 parts by mass |
| 4-n-butyl resorcinol | 0.3 parts by mass |
| Polymethacryloyllysine | 0.1 parts by mass |
| Polymethacryloyloxyethylphosphorylcholine | 0.1 parts by mass |
| Poly(glucosyloxyethyl methacrylate) | 0.1 parts by mass |
| Water | 83.75 parts by mass |

Example 5 and Comparative Example 5

In the same manner as in Example 1, but according to the following prescription, Lotion 5 as an external preparation for skin according to the present invention was produced. In the same manner, a lotion 5' of Comparative Example 5 in which 4-n-butyl resorcinol in Lotion 5 was substituted with ascorbic acid phosphate dipotassium which was used in conventional whitening cosmetics as a whitening agent was produced. Those lotions were given to five volunteer panelists (Japanese) who were troubled with dark-complexion, and Lotion 5 was used for the right-half face and the lotion 5' of Comparative Example 5 was used for the left-half face twice a day for 80 consecutive days. Munsell values of skin of them are shown in Table 7. Color tone was measured with Spectrophotometer CD 100, manufactured by Yokogawa M&C Corporation. As a result, Value was improved to 6 to 7 in each of the right-half faces and as to Hue a healthy skin color had been kept. On the contrary, Value was not sufficiently improved in each of the left-half faces and/or Hue of the skin was out of the range of that of a healthy skin. This shows that the external preparation for skin according to the present invention has whitening action that gives natural-looking appearance and is suitable for a lightening cosmetic.

| | |
|---|---|
| 1,2-hexanediol | 3 parts by mass |
| 1,3-butanediol | 5 parts by mass |
| Glycerin | 2 parts by mass |
| phenoxyethanol | 0.5 parts by mass |
| Compound 1 | 0.05 parts by mass |
| Polyoxyethylene hydrogenated castor oil | 0.1 parts by mass |
| Ethanol | 5 parts by mass |
| 4-n-butyl resorcinol | 2 parts by mass |
| Polymethacryloyllysine | 0.1 parts by mass |
| Polymethacryloyloxyethylphosphorylcholine | 0.1 parts by mass |
| Water | 82.15 parts by mass |

TABLE 7

Whitening Action of the Lotion 5

| | Right-half face (Lotion 5) | | | Left-half face (Lotion 5') | | |
|---|---|---|---|---|---|---|
| Panelists | Value | Hue | Chroma | Value | Hue | Chroma |
| A | 6.1 | 4.7 YR | 3.7 | 5.4 | 4.8 YR | 3.8 |
| B | 6.3 | 4.9 YR | 3.5 | 5.7 | 5.1 YR | 3.5 |
| C | 6.0 | 4.7 YR | 3.6 | 5.7 | 4.6 YR | 3.7 |
| D | 6.2 | 4.9 YR | 3.5 | 5.9 | 5.1 YR | 3.5 |
| E | 6.1 | 4.7 YR | 3.5 | 5.9 | 4.9 YR | 3.6 |

Comparative Example 6

In the same manner as in Example 5, a lotion 6 of Comparative Example 6 in which 4-n-butyl resorcinol in Lotion 5 was substituted with arbutin which was used in conventional whitening cosmetics as a whitening agent was produced. Those lotions were given to five volunteer panelists (Japanese) who were troubled with dark-complexion, and Lotion 5 was used for the right-half face and the lotion 6 of Comparative Example 6 was used for the left-half face twice a day for 80 consecutive days. Munsell values of skin of them are shown in Table 8. Color tone was measured with Spectrophotometer CD 100, manufactured by Yokogawa M&C Corporation. As a result, Value was improved to 6 to 7 in each of the right-half faces and as to Hue a healthy skin color had been kept. On the contrary, Value was not sufficiently improved in each of the left-half faces and/or Hue of the skin was out of the range of that of a healthy skin. This shows that the external preparation for skin according to the present invention has whitening action that gives natural-looking appearance and is suitable for a lightening cosmetic.

TABLE 8

Whitening Action of Lotion 5

| | Right-half face (Lotion 5) | | | Left-half face (Lotion 6) | | |
|---|---|---|---|---|---|---|
| Panelists | Value | Hue | Chroma | Value | Hue | Chroma |
| A | 6.2 | 4.8 YR | 3.5 | 6.0 | 5.2 YR | 3.6 |
| B | 6.1 | 4.9 YR | 3.9 | 5.8 | 5.2 YR | 3.9 |
| C | 6.0 | 4.8 YR | 3.7 | 5.8 | 5.1 YR | 3.8 |
| D | 6.3 | 4.9 YR | 3.3 | 5.9 | 5.0 YR | 3.4 |
| E | 6.1 | 4.8 YR | 3.7 | 5.9 | 4.7 YR | 3.7 |

INDUSTRIAL APPLICABILITY

The present invention can be applied to a whitening cosmetic that realizes natural-looking beautifulness (whiteness).

What is claimed is:

1. An external preparation for skin, comprising one or more compound(s) selected from 5,7-dihydroxy-3,6-dimethoxy-2-(5-hydroxy-4-methoxyphenyl)-4H-1-benzopyran-4-one, 5,7-dihydroxy-3,6,8-trimethoxy-2-(3,4,5-trihydroxyphenyl)-4H-1-benzopyran-4-one, and 3,5-diethoxy-6,7-dimethoxy-2-(5-ethoxy-4-methoxyphenyl)-4H-1-benzopyran-4-one and/or a salt thereof in a range of 0.035 to 2.0% by mass; and 4-n-butyl resorcinol and/or a salt thereof in a range of 0.05 to 5% by mass.

2. The external preparation for skin according to claim 1, wherein a source of the compound and/or salt thereof is an extract of a plant of the genus *Achillea* sp. of the family Compositae or the genus *Centaurea* sp. of the family Compositae.

3. The external preparation for skin according to claim 2, wherein the plant of the genus *Achillea* sp. of the family Compositae is selected from *Achillea ageratum, Achillea cartilaginea, Achillea clavenae, Achillea filipendula, Achillea millefolium, Achillea nana, Achillea ptarmica*, and *Achillea tomentosa*, and the plant of the genus *Centaurea* sp. of the family Compositae is *Centaurea cyanus*.

4. A method for whitening skin comprising applying the external preparation for skin according to claim 1 to the skin of an individual, whereby the skin of the individual is whitened.

5. A method for lightening skin comprising applying the external preparation for skin according to claim 1 to the skin of an individual, whereby the skin of the individual is lightened.

* * * * *

UNITED STATES PATENT AND TRADEMARK OFFICE
CERTIFICATE OF CORRECTION

| | |
|---|---|
| PATENT NO. | : 7,795,300 B2 |
| APPLICATION NO. | : 10/580882 |
| DATED | : September 14, 2010 |
| INVENTOR(S) | : Tada et al. |

Page 1 of 1

It is certified that error appears in the above-identified patent and that said Letters Patent is hereby corrected as shown below:

Column 4, Line 65, "ketone nitrites such as" should be changed to --ketone nitriles such as--

Column 5, Line 53, "PRODUCTION EXAMPLE 1 TO 5" should be changed to --PRODUCTION EXAMPLES 1 TO 5--

Column 8, Line 28, "sorbit fattyacidesters" should be changed to --sorbit fatty acid esters--

Signed and Sealed this
Twelfth Day of April, 2011

David J. Kappos
*Director of the United States Patent and Trademark Office*